United States Patent [19]
Nunogaki

[11] Patent Number: 4,968,428
[45] Date of Patent: Nov. 6, 1990

[54] CENTRIFUGAL COUNTER-CURRENT DISTRIBUTION CHROMATOGRAPHY

[75] Inventor: Yoshiaki Nunogaki, Nagaokakyo, Japan

[73] Assignee: Sanki Engineering, Ltd., Kyoto, Japan

[21] Appl. No.: 400,054

[22] Filed: Aug. 29, 1989

Related U.S. Application Data

[60] Division of Ser. No. 326,498, Mar. 20, 1989, Pat. No. 4,877,523, which is a continuation of Ser. No. 120,313, Nov. 13, 1987, abandoned.

[51] Int. Cl.$^5$ .............................................. B01D 15/08
[52] U.S. Cl. .................................. 210/635; 210/657; 422/70; 436/161
[58] Field of Search ............ 210/635, 657, 198.2, 210/198.3; 422/70; 436/161

[56] References Cited

U.S. PATENT DOCUMENTS

| | | | |
|---|---|---|---|
| 4,051,025 | 9/1977 | Ito | 210/657 |
| 4,324,661 | 4/1982 | Ito | 210/657 |
| 4,551,251 | 11/1985 | Kolobow | 210/657 |
| 4,632,762 | 12/1986 | Ramsland | 210/657 |

FOREIGN PATENT DOCUMENTS

| | | | |
|---|---|---|---|
| 56-16868 | 2/1981 | Japan | 422/70 |
| 58-1386 | 1/1983 | Japan | 210/198.2 |

*Primary Examiner*—Ernest G. Therkorn
*Attorney, Agent, or Firm*—Wenderoth, Lind & Ponack

[57] ABSTRACT

A cassette for use in a centrifugal counter-current distribution chromatographic apparatus which comprises a motor-driven rotor supported for rotation about a shaft having at least one pocket defined therein, and at least one cassette having a tortuous separation passage defined therein with the opposite ends adapted to be connected respectively to a source of fluid samples and the outside, the fluid samples being continuously supplied to the separation passage while the rotor is driven in one direction at high speed to effect the counter-current distribution. The cassette comprises at least one flat plate member having defined therein a plurality of slots and a corresponding number of narrow grooves alternating with the slots, each of the narrow grooves being continued at one end to one slot and at the other end to the next adjacent slot, sealing plates disposed on respective side faces of the flat plate member, and metallic side plates clamped together with the flat plate member and the sealing plates disposed therebetween. The slots and narrow grooves are so defined in the flat plate member that, when the cassette is mounted on the rotor, they can be oriented radially of the rotor.

2 Claims, 8 Drawing Sheets

CENTRIFUGAL COUNTER-CURRENT DISTRIBUTION CHROMATOGRAPHY

This is a Rule 60 Divisional application of Ser. No. 326,498 filed Mar. 20, 1989, now U.S. Pat. No. 4,877,523 which in turn is a continuation of Ser. No. 120,313, filed Nov. 13, 1987, and now abandoned.

BACKGROUND OF THE INVENTION 1. (Field of the Invention)

The present invention generally relates to the art of centrifugal counter-current distribution chromatography and, more particularly, to an apparatus for carrying out the centrifugal counter-current distribution chromatography for the assay and the separation and purification, i.e. for the quantitative or qualitative analysis, of biochemical substances or natural organic compounds, and also for the refinement of crude samples.

2. (Description of the Prior Art)

When centrifugal counter-current distribution chromatography is continuously performed, if the stationary phase liquid and the mobile phase liquid are mixed and separated while centrifugally accelerated, the time required to complete the separation and the assay can be remarkably reduced and the limitation imposed by the distribution liquid system can be alleviated. Numerous apparatuses for performing centrifugal counter-current distribution based on this idea have been proposed, all of which make use of a coiled separation tube disposed in a centrifuge for facilitating the separation. The use of a coiled separation tube present a problem in that, if the quantity of the sample to be separated and analyzed is increased, the coiled separation tube must have a correspondingly increased inner diameter. As the inner diameter of the coiled separation tube increases the distribution of substances between, the mobile phase liquid and the stationary phase liquid correspondingly decrease, accompanied by an increased spread of the separation peak resulting from the diffusion. In view of this, the amount of samples that can be separated and processed with the coiled separation tube has been limited accordingly.

The assignee of the present invention has disclosed a centrifugal counter-current distribution chromatographic apparatus, which has successfully alleviated the above-discussed problems, in Japanese Patent Publication No. 58-1386, published in 1983. According to this publication, there is disclosed a cassette comprising a single separation passage and adapted to be detachably mounted on an outer peripheral portion of a motor-driven rotor, such as illustrated in FIGS. 17 to 20 of the accompanying drawings.

The prior art cassette disclosed in the above-mentioned publication and generally identified by 1 in FIGS. 17 to 20 comprises a generally elongated and generally rectangular cross-sectioned body 2 made of synthetic resin and having first and second opposite side faces to which respective metal side plates 3 are secured through sealing plates 4 by means of fastening members such as, for example, set screws. The elongated body 2 has defined therein a plurality of, for example two rows of, large-diameter bores 5a and 5b and an equal number of rows of small-diameter bores 6a and 6b. Each of the large-diameter bores 5a and 5b of each row extends substantially perpendicular to the longitudinal -axis of the elongated body 2 with its opposite ends open to the first and second side faces of the elongated body 2 and, similarly, each of the small-diameter bores 6a and 6b of each row extends substantially perpendicular to the longitudinal axis of the elongated body 2 with its opposite ends open to the first and second side faces of the elongated body 2. The large-diameter bores 5a and 5b and the small-diameter bores 6a and 6b communicate at their opposite ends, with each other through respective transverse grooves 7 defined in the first and second side faces of the elongated body 2 whereby, when the sealing plates 4 are respectively secured to the first and second side faces of the elongated body 2, a generally tortuous single separation passage extending from an inlet port 8 to an outlet port 9, which are both open at an upper end region of the first side face of the elongated body 2, is formed in the cassette 1. The tortuous passage so defined in the cassette 1 has a series of small-diameter passage portions, defined by the small-diameter bores 6a and 6b and the transverse grooves 7, and a series of large-diameter passage portions defined by the large-diameter bores 5a and 5b, said series of small-diameter and large-diameter passage portions alternately disposed over the entire length of the tortuous separation passage.

When in use, the cassette 1 having the construction described above is mounted on the motor-driven rotor with the small-diameter and large-diameter passage portions, that is, the small-diameter and large-diameter bores 6a, 6b and 5a, 5b, oriented in a radial direction radially of the motor-driven rotor and parallel to the direction in which a centrifugal force acts during high speed rotation of the motor-driven rotor. The inlet port 8 and the outlet port 9 respectively communicate with a source of a liquid medium to be examined and a collecting vessel through associated collets 10 and 11 to which suitable lengths of tubing are connected.

According to the prior art cassette 1, not only can a relatively large number of theoretically effective stages be employed, but also the volume of the stationary phase liquid retained in each of the large-diameter passage portions, that is, each of the large-diameter bores 5a and 5b, can be advantageously increased with a resulting increase of the ratio of volume between the stationary phase liquid and the mobile phase liquid. Because of these advantages, the use of the cassette 1 having the construction shown in and described with reference to FIGS. 17 to 20 is effective to accomplish the separation of samples in a reduced amount of time.

However, it has been found that the prior art cassette for use in centrifugal counter-current distribution chromatography is very complicated and, therefore, costly to fabricate. More specifically, not only is a time-consuming and complicated drilling operation required to form the enormous number of large-diameter and small-diameter bores in the elongated body, but also these large-diameter and small-diameter bores must be accurately positioned relative to each other, requiring a highly precise machining technique. Therefore, the prior art cassette is costly to fabricate and is, therefore, high-priced.

SUMMARY OF THE INVENTION

Accordingly, the present ,invention has been devised to substantially eliminate the above-discussed problems inherent in the prior art cassette and has as its essential object to provide a centrifugal counter-current distribution chromatographic apparatus wherein a cassette has separation passages each defined by alternately disposed small-diameter and large-diameter passage portions which can be fabricated easily and inexpensively by the employment of a simple manufacturing process.

In order to accomplish the above-described object, the present invention is drawn to a cassette which comprises at least one flat plate member having defined therein a plurality of slots and a corresponding number of narrow grooves alternately disposed with said slots, each of said narrow grooves being open at one end to one slot and at the other end to an adjacent slot, sealing plates disposed on respective side faces of the flat plate member, and metallic side plates clamped together with the flat plate member and the sealing plates disposed therebetween, said slots and narrow grooves being so defined in the flat plate member that, when the cassette is mounted in the pocket in the rotor, they are oriented radially in the rotor.

In this assembled condition, the slots and the narrow grooves form, respectively, a series of generally elongated chambers and a series of narrow channels alternating with the elongated chambers, each of said narrow channels communicating at one end with one elongated chamber and at the opposite end with an adjacent elongated chamber.

According to another preferred embodiment, there is provided a rotor comprising at least one disc-shaped flat plate member having defined therein a plurality of slots and a corresponding number of narrow grooves alternating with said slots, each of said narrow grooves being open at one end to one slot and at the other end to an adjacent slot, sealing plates disposed on respective surfaces of the flat plate member, and metallic side plates clamped together with the flat plate member and the sealing plates disposed therebetween. In this assembled condition, the slots and the narrow grooves form, respectively, a series of generally elongated chambers and a series of narrow channels alternating with the elongated chambers, each of said narrow channels communicating at one end with one elongated chamber and at the opposite end with an adjacent elongated chamber.

BRIEF DESCRIPTION OF THE DRAWINGS

This and other objects and features of the present invention will become clear from the following description taken in conjunction with preferred embodiments thereof with reference to the accompanying drawings, in which.

DETAILED DESCRIPTION OF THE PREFERRED EMBODIMENTS

Figure 1:
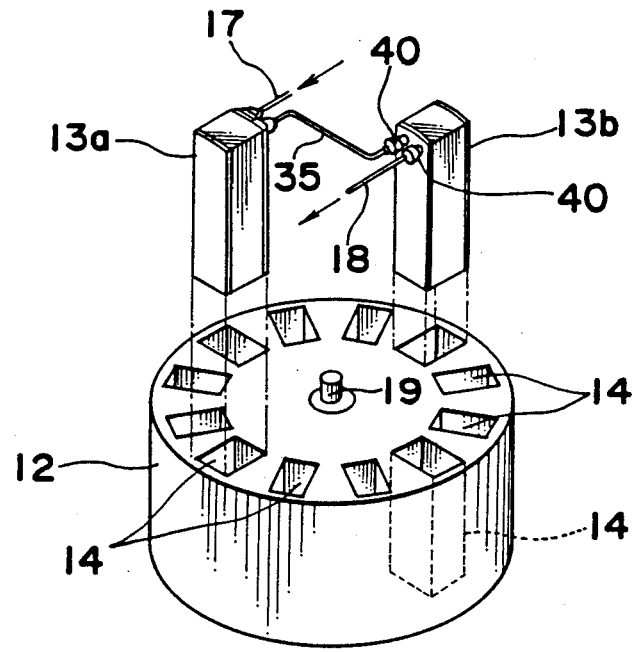
FIG. 1 is a schematic perspective view showing cassettes ready to be mounted on a motor-driven rotor according to a first preferred embodiment of the present invention.
Figure 2:
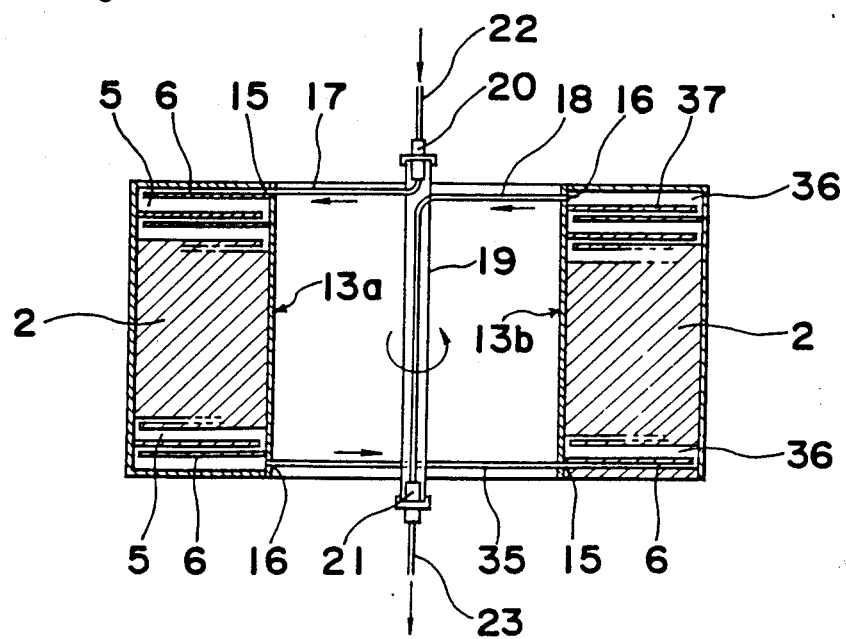
FIG. 2 is a side sectional view of the motor-driven rotor having the cassettes mounted thereon.
Figure 3:
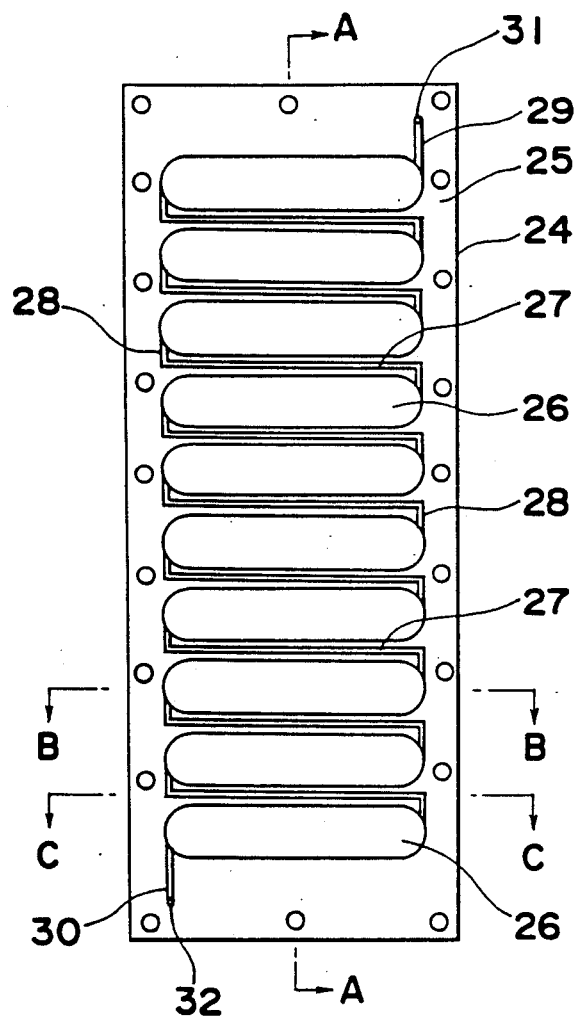
FIG. 3 is a plan view showing, on an enlarged scale, one passage defining member which is a component part of each of the cassettes according to the first embodiment of the present invention.
Figure 4:
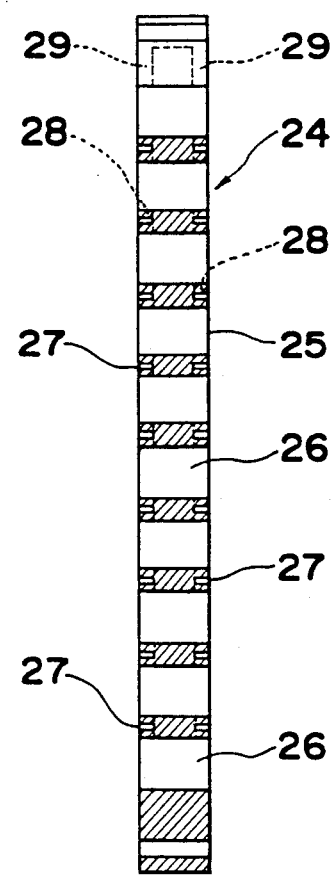
FIGS. 4 to 6 are cross-sectional views taken along the lines A—A, B—B and C—C in FIG. 3, respectively.
Figure 5:
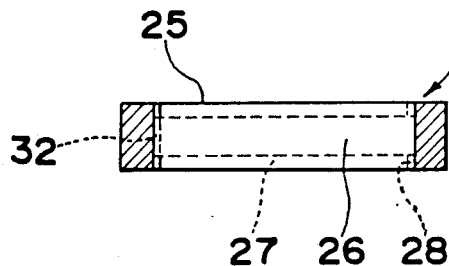
Figure 6:
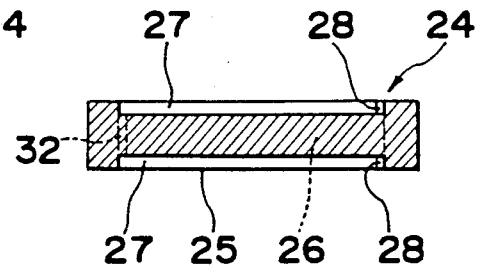

Referring first to FIGS. 1 and 2, one or more, for example, two, cassettes 13a and 13b are shown as being mounted on a motor-driven rotor 12 forming a part of a centrifugal counter-current distribution chromatographic apparatus. The motor-driven rotor 12, generally cylindrical in shape, has a plurality of cassette receiving pockets, 14 defined in a peripheral portion thereof and extending in a direction parallel to a shaft 19 defining the axis of rotation of the rotor 12, said pockets 14 being spaced an equal distance from shaft 19 in a radial direction of the rotor 12 and from each other in a circumferential direction of the rotor 12. For purposes to be described later, the shaft 19 has upper and lower free ends thereof provided with respective rotary couplings 20 and 21 as best shown in FIG. 2.

A cassette may be inserted in each of the cassette receiving pockets 14 when the apparatus is in use. However, when two cassettes 13a and 13b having identical constructions such as those shown are used, they should be inserted in two of the pockets 14 which are circumferentially opposite to each other, that is, which are spaced 180° from each other with respect to the shaft 19.

Each of the cassettes 13a and 13b has a generally tortuous separation passage defined therein and extending from an inlet port 15 to an outlet port 16, said inlet and outlet ports 15 and 16 being arranged in a side-by-side fashion and facing in the same direction. With the cassettes 13a and 13b so inserted into the respective pockets 14 in the motor-driven rotor 12, the outlet port 16 of one of the cassettes 13a and 13b is fluid-connected with the inlet port 15 of the other of the cassettes 13a and 13b. The inlet port 15 of such one of the cassettes 13a and 13b is fluid-connected by means of a suitable tubing 17 with the rotary coupling 20 which is in turn fluid-connected with a supply line 22, and the outlet port 16 of such other of the cassettes 13a and 13b is fluid-connected by means of suitable tubing 18 with the rotary coupling 21 which is in turn fluid-connected with a discharge line 23.

Each cassette according to the present invention comprises one or more generally plate-like passage defining members connected together in a face-to-face relationship with a sealing plate interposed between adjacent passage defining members. While the manner in which the cassette is assembled will be described later, the details of each of the passage defining plates will first be described with particular reference to FIGS. 3 to 6.

The passage defining member is generally identified by 24 and comprises a generally rectangular flat plate 25 having a plurality of, for example, ten, slots 26 extending therein parallel to each other and in a direction widthwise of the flat plate 25 and spaced an equal distance from each other. The flat plate 25 also has a plurality of grooves 27 defined on each of the opposite surfaces thereof, each of said grooves 27 extending between adjacent ones of the slots 26 and having a width smaller than that of any one of the slots 26. The slots 26 and the grooves 27 alternately communicate with each other through associated connecting grooves 28 each formed on respective surface of the flat plate 25 so as to connect one of the opposite ends of one slot 26 with adjacent one of the opposite ends of the groove 27 adjacent such one slot 26.

The flat plate 25 has two bores 31 and 32 defined at opposite ends thereof, each of said bores 31 and 32 extending completely therethrough. The bore 31 is connected to one end of the uppermost slot 26, as viewed in FIGS. 3 and 4, through connecting grooves 29 defined on the respective surfaces of the flat plate 25 adjacent the upper end thereof, whereas the bore 32 is connected to the opposite end of the lowermost slot 26 through connecting grooves 30 defined on the respective surfaces of the flat plate 25 adjacent the lower end thereof. It is to be noted that the connecting grooves 29 and the bore 31 communicating therewith are positioned so as to assume an offset relationship with the connecting groove 30 and the bore 32, communicating therewith, with respect to the longitudinal axis of the flat plate 26.

Figure 7:
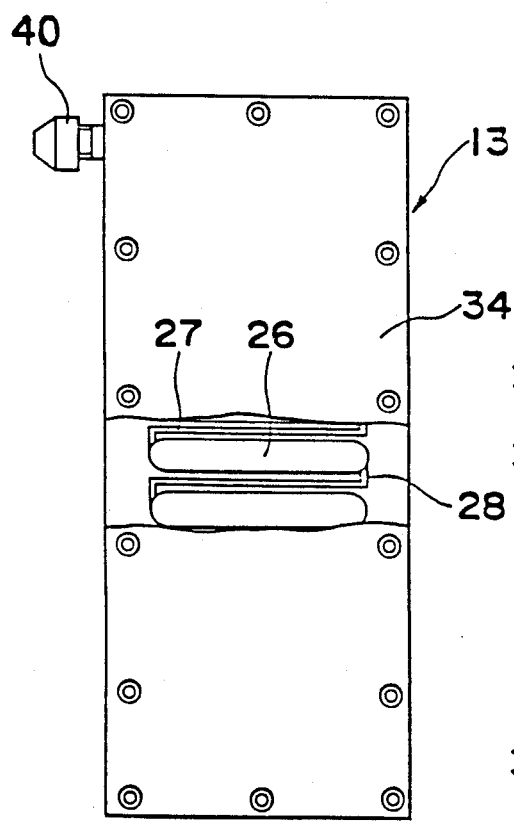
FIG. 7 is a plan view showing, on an enlarged scale, one of the cassettes, with a portion cut away, according to the first embodiment of the present invention.
Figure 8:
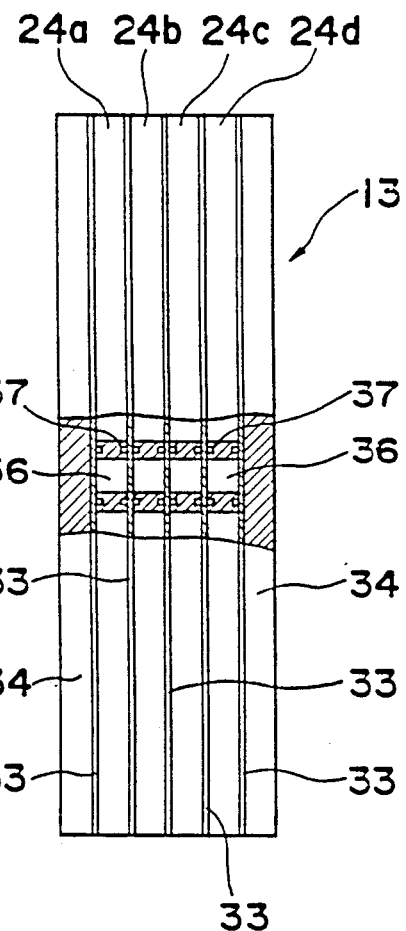
FIG. 8 is a side view of the cassette shown in FIG. 7 with a portion cut away.

The cassette now generally identified by 13 in FIGS. 7 and 8 is formed by connecting a plurality of, for example, four, plate-like passage defining members 24a, 24b, 24c and 24d, each comprising structure which has been described with reference to FIGS. 3 to 6, together, in a face-to-face relationship with a sealing plate 33 interposed between adjacent passage defining members, which members 24a to 24d are in turn clamped between metallic side plates 34 by a plurality of set screws extending from one metallic side plate 34 to the other metallic side plate 34 across members 24a to 24d. Preferably, a sealing plate 33 is interposed between each metallic side plate 34 and the body of the passage defining members 24a to 24d as best shown in FIG. 8.

Figure 9:
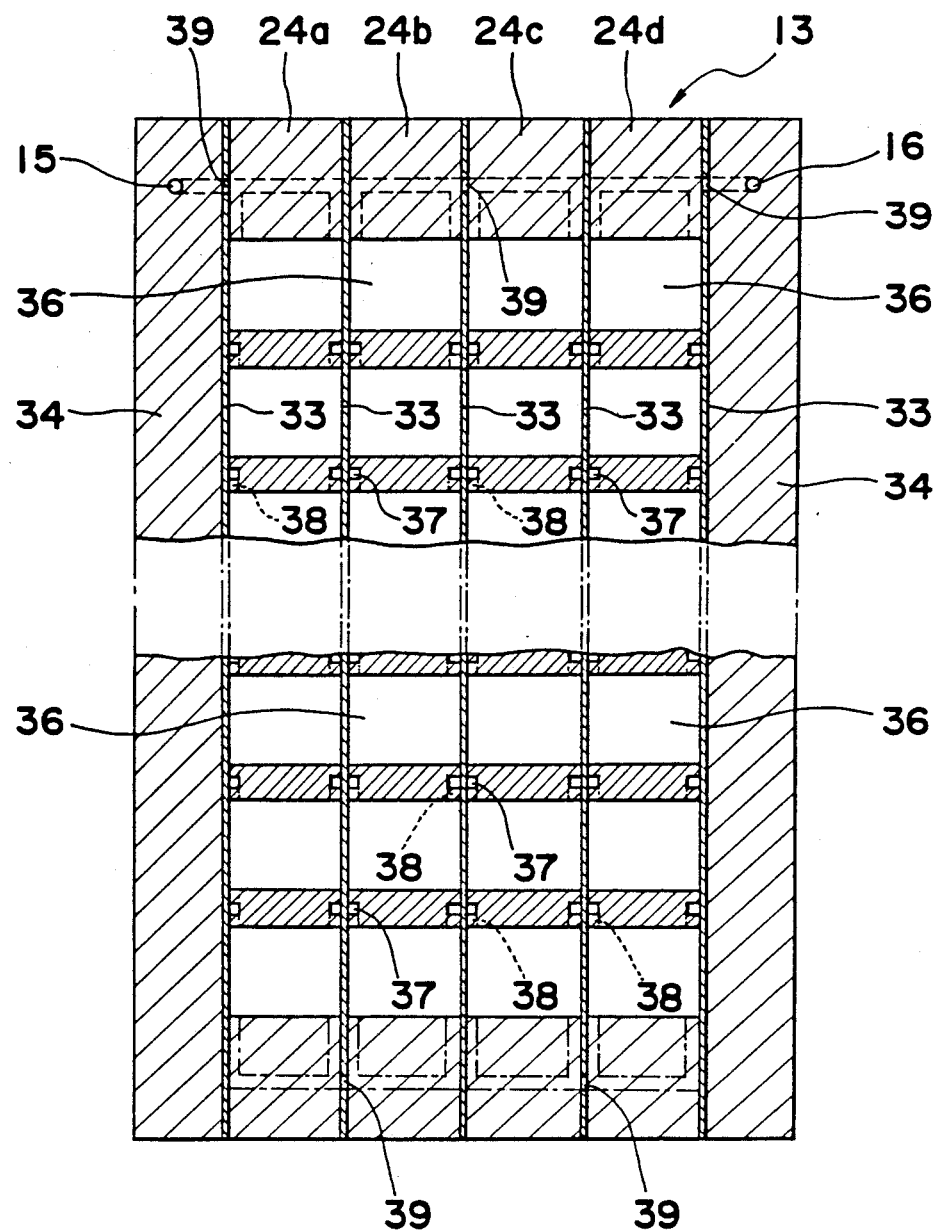
FIG. 9 is a fragmentary side sectional view, on a further enlarged scale, of the cassette shown in FIG. 7.

When the passage defining members 24a to 24d are assembled together between the metallic side plates 34 with the sealing plates 33 interposed in the manner as described hereinabove and as shown in FIGS. 8 and 9, the slots 26 and the paired grooves 27 in each passage defining member 24a to 24d are confined by the adjoining sealing plates 33 on the respective sides of such passage defining plate 24 to define, respectively, the elongated chambers 36 and the paired channels 27 alternately disposed one above the other. Each channel 27 so defined communicates at one end with one of the opposite ends of one chamber 36 and at the other end with the other of the opposite ends of an adjacent chamber 36 through a respective connecting duct 38 that is similarly defined by the respective connecting groove 28 when the latter is confined by the adjacent sealing plate 33.

Thus, it is clear that a generally zigzag-shaped fluid flow path comprised of the elongated chambers 36 alternating with and fluid-connected with the paired channels 27 extends from the bore 31 to the bore 32 in each passage defining member 24a to 24d.

In the illustrated embodiment in which the four passage defining members 24a to 24d are employed, four zigzag-shaped fluid flow paths are provided one in each passage defining member 24a to 24d, and all of which communicate in series through connecting ducts 39 alternately defined in upper and lower ends of the associated sealing plates 33, each of said connecting ducts 39 extending completely through the sealing plates 33, thereby completing the single separation passage extending from the bore 31 in the leftmost passage defining member 24a to the bore 31 in the rightmost passage defining member 24d as viewed in FIGS. 8 and 9. The bore 31 in the leftmost passage defining member 24a communicates with the collet 40 through the supply port 15 defined in the leftmost metallic side plate 34, and the bore 31 in the leftmost passage defining member 24d is communicates with the collet 40 through the discharge port 16 defined in the rightmost passage defining member 14d.

Referring back to FIGS. 1 and 2, each of the cassettes 13a and 13b comprising the structure which has been described with reference to FIGS. 3 to 9, are mounted on the rotor 12 in the manner as hereinbefore described. At this time, the elongated chambers 36 in each of the cassettes 13a and 13b extend radially of the rotor 12 with their longitudinal axes disposed perpendicular to the axis of rotation of the rotor 12. It is to be noted that the length of, each of the elongated chambers 36 is selected so as not to be greater than half the radius of the rotor 12 so that, if the centrifugal acceleration measured at the outer periphery of the rotor is expressed by G, the average centrifugal acceleration measured inside the elongated chambers 36 is not smaller than three fourths of G.

Figure 10:
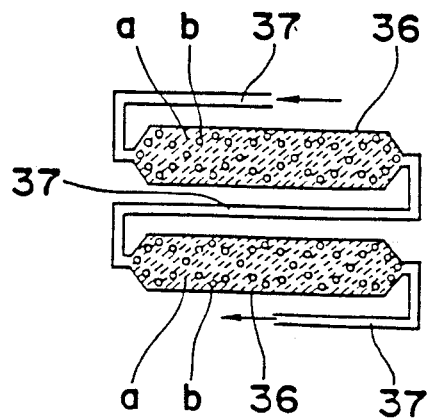
FIG. 10 is a schematic diagram showing a portion of the tortuous separation passage defined in the cassette.

The operation of the apparatus of the construction according to the foregoing embodiment will now be described with particular reference to FIGS. 2 and 10.

At the outset, the tortuous separation passage in each of the cassettes 13a and 13b, including the elongated chambers 36 and the channels 37, is filled with a quantity of stationary phase liquid a having a high specific gravity. Thereafter, a drive motor (not shown) is driven to rotate the rotor 12 at a high speed about the shaft 19 while a mobile phase liquid b is pumped through a supply piping 22 via the rotary coupling 20 so as to flow into one of the cassettes 13a through the tubing 17 thereby to initiate the countercurrent distribution. In other words, the mobile phase liquid supplied through the inlet port 15 flows into the elongated chambers 36 from respective ends of the channels 37, which are farthest from the shaft 19 against the stationary phase liquid a. Since at this time a greater centrifugal force acts on the stationary phase liquid a having a high specific gravity than on the mobile phase liquid having a low specific gravity, the mobile phase liquid b breaks up into fine particles as shown in FIG. 10 moving in a direction counter to the direction in which the centrifugal force acts, that is, in a direction rightwards as viewed in FIG. 10, resulting in a distribution and separation taking place between the mobile phase liquid b and the stationary phase liquid a. At the same time, the particles of the mobile phase liquid b pass through the elongated chambers 36 without being biased, because the elongated chambers 36 are oriented radially of the rotor 12.

The mobile phase liquid b which has passed through the stationary phase liquid a is collected at each inner end face of the elongated chambers 36 and is then centrifugally purged into the channels 37 through the connecting ducts 38. The counter-current distribution is repeated in this way until equilibrium is established. When equilibrium is established, the stationary phase liquid a is retained within the elongated chambers 36 and the mobile phase liquid b fills up the channels 37. In this condition, four fifths of the total volume in the cassettes 13a and 13b is occupied by the stationary phase liquid a and the remaining one fifths of the total volume is occupied by the mobile phase liquid b. The mobile phase liquid b which has been fractioned as a result of the passage thereof through the cassettes 13a and 13b is discharged through the tubing 18, then the rotary coupling 21 and finally through a discharge piping 23.

In the above described cassettes 13a and 13b, because the elongated chambers 36 alternating with the channels 37 define a single tortuous separation passage, not only can a relatively large number of theoretically effective stages be employed, but also the volume of the stationary phase liquid retained in each of the elongated chambers 36 can be advantageously increased with the consequent increase of the ratio of volume between the stationary phase liquid and the mobile phase liquid. Because of these advantages, the separation of samples can be accomplished in a reduced amount of time.

It is to be noted that, while in the foregoing description each groove 27 which eventually forms the respective channel 37 has been described as formed on each of the opposite surfaces of the associated passage defining flat plate 25, such may be formed on only one surface of the respective passage defining flat plate 25.

From the foregoing description, it is clear that, since in the centrifugal counter-current distribution chromatographic apparatus according to the foregoing embodiment each cassette is formed by laminating a plurality of passage defining members, each formed with the slots and the relatively narrow grooves alternating with and open to the slots, with the the sealing plates interposed so that the slots and the narrow grooves form elongated chambers and channels connected together in an alternating manner to define the separation passage, a cassette capable of completely separating as many varieties of samples as possible in a time as short as possible can be fabricated only by laminating the passage defining members which can be formed of synthetic resin to have identical shapes with the use of any known molding technique and, therefore, the cassette can be easily and inexpensively manufactured wherefore the cassette can be made available in the market at a reduced price.

Hereinafter, a second preferred embodiment of the present invention will be described with reference to FIGS. 11 to 14.

Figure 11:
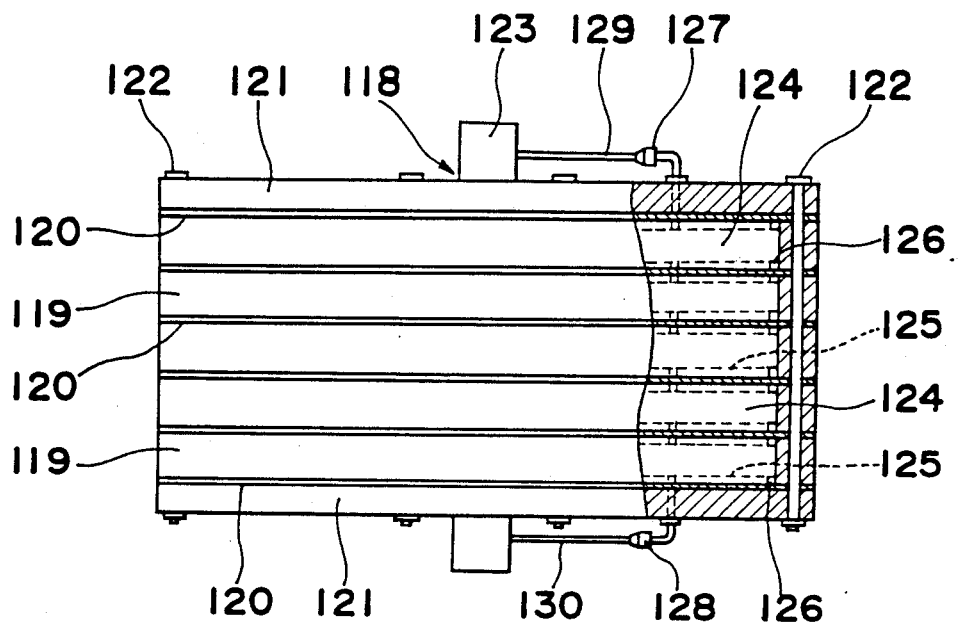
FIG. 11 is a front elevational view, with a portion shown in section, of the centrifugal counter-current distribution chromatographic apparatus according to a second preferred embodiment of the present invention.

As shown in FIG. 11, a generally drum-shaped rotor 118 has a generally tortuous separation passage defined therein and extending from an inlet port 121' to an outlet port 121" located at the top and bottom of the rotor 118, respectively. The drum-shaped rotor 118 shown therein is formed by stacking a plurality of, for example, five, generally circular passage defining members, each identified by 119, one above the other with a disc-shaped sealing plate 120 interposed between adjacent passage defining members, which members 119 are in turn clamped between metallic side plates 121 with a plurality of set bolts 122 extending from one metallic side plate 121 to the other metallic side plate 121 across the stack of members 119. Preferably, a similar sealing plate 120 is interposed between each metallic side plate 119 and the stack of the passage defining members 119 as best shown in FIG. 11.

The details of each of the passage defining members 119 will first be described with particular reference to FIGS. 13 and 14.

Each passage defining member 119 comprises a disc plate 119a made of synthetic resin having a central hole 119b for receiving the passage of a shaft 123 therein and also a plurality of slots 119c having equal lengths extending radially therein and spaced equal distances from each other in a circumferential direction thereof, each of said slots 119c having a width that progressively increases in a radially outwardly extending direction of the disc plate 119a. The disc plate 119a further has a plurality of narrow grooves 119d defined on respective opposite surfaces of the disc plate 119a, each of said grooves 119d being located between the adjacent ones of the slots 119c and having a width sufficiently smaller than that of any one of the slots 119c. The slots 119c and the paired grooves 119d alternately communicate with each other through associated connecting grooves 119e each formed on a respective surface of the disc plate 119a so as to connect one of the opposite ends of one slot 119c with the adjacent one of the opposite ends of the groove 119d adjacent such one slot 119c.

The disc plate 119a has supply and outflow grooves 119f and 119g formed on the respective opposite surfaces thereof each of said grooves 119f and 119g having a length substantially equal to half the length of any one of the paired grooves 119d, and concentric inner and outer circular rows of bearing holes 123 for receiving the connecting bolts 122 and which are defined adjacent the radially outer and inner ends of the slots 119c and the grooves 119d.

Figure 12:
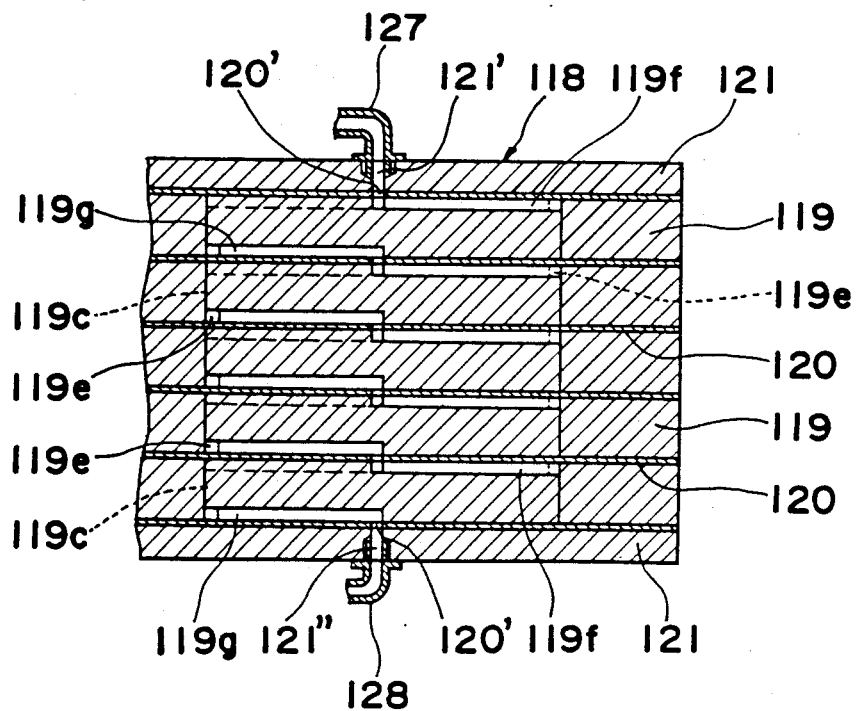
FIG. 12 is a sectional view, on an enlarged scale, of a portion of the apparatus shown in FIG. 11.
Figure 13:
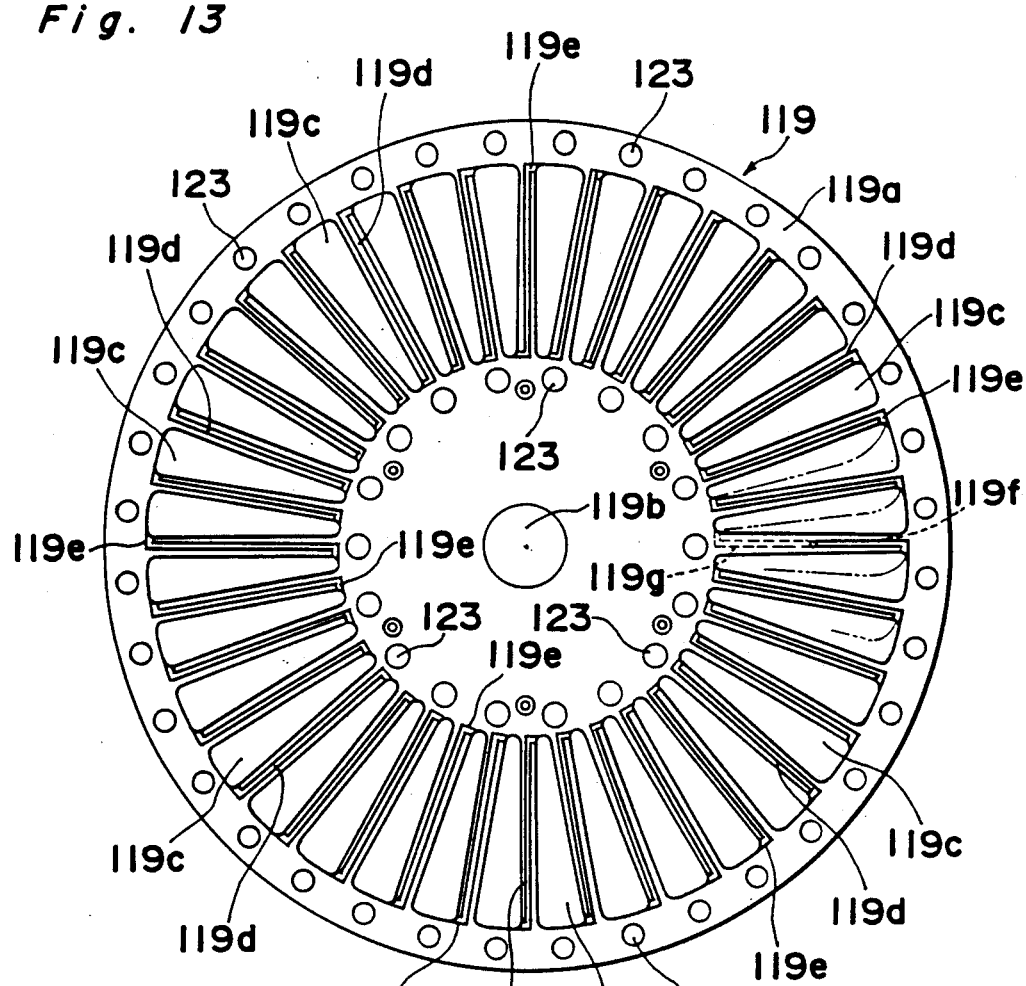
FIG. 13 is a top plan view, on an enlarged scale, of a passage defining disc used in the apparatus shown in FIG. 11.
Figure 14:
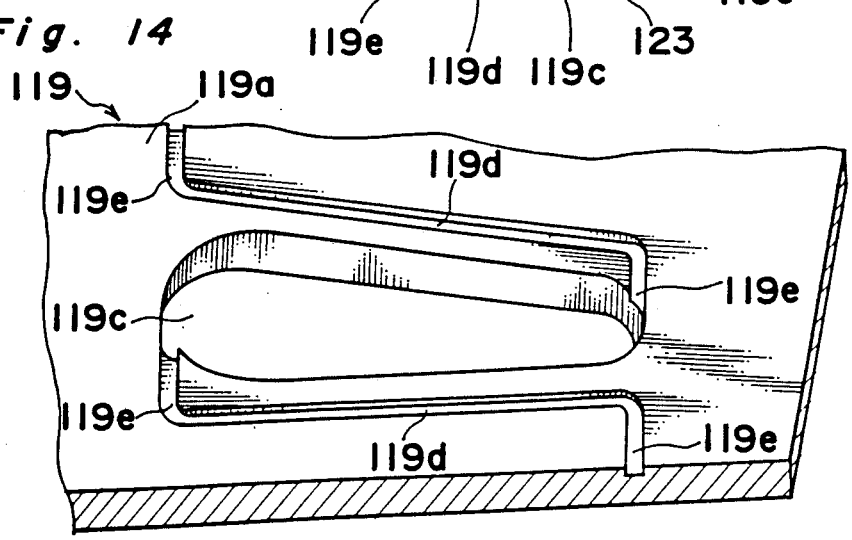
FIG. 14 is a perspective view, on a further enlarged scale, showing a portion of the passage defining disc shown in FIG. 13.

As best shown in FIG. 12, a plurality of the disc plates 119a each being constructed as shown in and described with reference to FIGS. 13 and 14 are stacked one above the other with the respective supply and outflow grooves 119f and 119g in one disc plate 119a aligned with those in an adjacent disc plate 119a and also with the the sealing plate 120 interposed between each pair of adjacent disc plates 119a, the assembly being clamped together between the metallic side plates 121 with the connecting bolts 122 passing through the inner and outer circular rows of the bearing holes 123. It is to be noted that, when the disc plates 119a and the sealing plates 120 are alternately stacked one above the other and clamped together, the inlet and outlet ports 121' and 121" are aligned with the inlet port 121' in the uppermost one of the disc plates 119a and the outlet port 121" in the lowermost one of the disc plates 119a.

Thus, when the passage defining members 119 are assembled together between the metallic side plates 121 with the sealing plates 120 interposed in the manner as described hereinabove and as shown in FIGS. 11 and 12, the slots 119c and the paired grooves 119d in each passage defining member 119 are confined by the adjoining sealing plates 120 on the respective sides of such passage defining plates 119 to define, respectively, the alternating elongated chambers 124 and the paired channels 125 positioned one above the other. Each channel 125 so defined communicates at an inner end thereof with an inner end of one chamber 124 and at the opposite, outer end hereof with the opposite, outer end of the adjacent chamber 124 through a respective connecting duct 126 that is similarly defined by the respective connecting groove 119e when the latter is confined by the adjacent sealing plate 120. Thus, it is clear that a generally zigzag-shaped fluid flow path comprised of the elongated chambers 124 alternating with and fluid-connected with the paired channels 125 extends from the bore 121' to the bore 121" in each passage defining member 119.

In the illustrated embodiment in which the five passage defining members 119 are employed, five zigzag-shaped fluid flow paths are provided one each in each passage defining member 119, and all of which communicate in series with each other through connecting ducts 120' defined in each sealing plate 120, each of said connecting ducts 120' extending completely through the sealing plate 120, thereby completing the single separation passage extending from the inlet port 121' in the uppermost passage defining member 119 to the outlet port 121" in the lowermost passage defining member 119 as viewed in FIGS. 11 and 12. The inlet port 121' in the uppermost passage defining member 119 communicates with the collet 127, and the outlet port 121" in the lowermost passage defining member 119 communicates with the collet 128.

Figure 15:
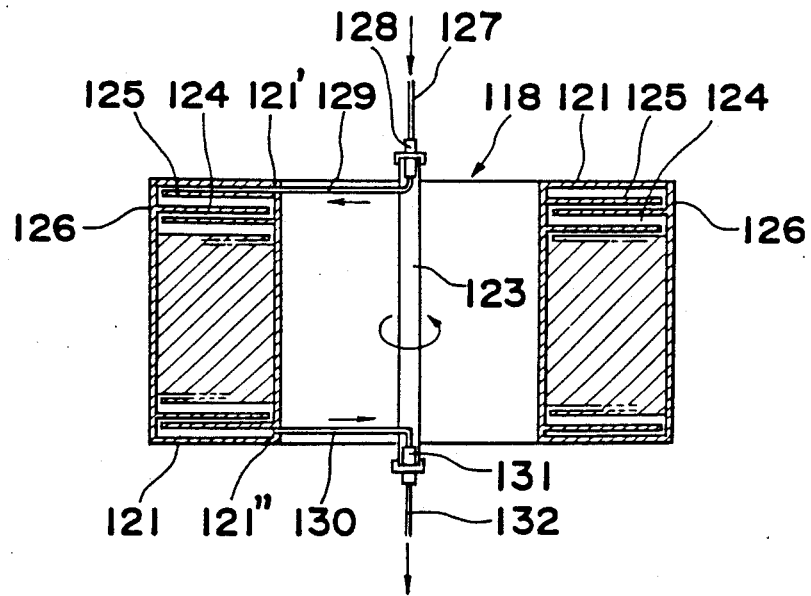
FIG. 15 is a schematic side sectional view of the apparatus illustrating the operation thereof.
Figure 16:
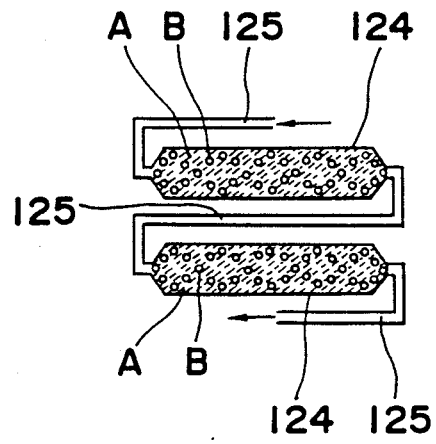
FIG. 16 is a diagram similar to FIG. 10, but pertaining to the second embodiment of the present invention.
Figure 17:
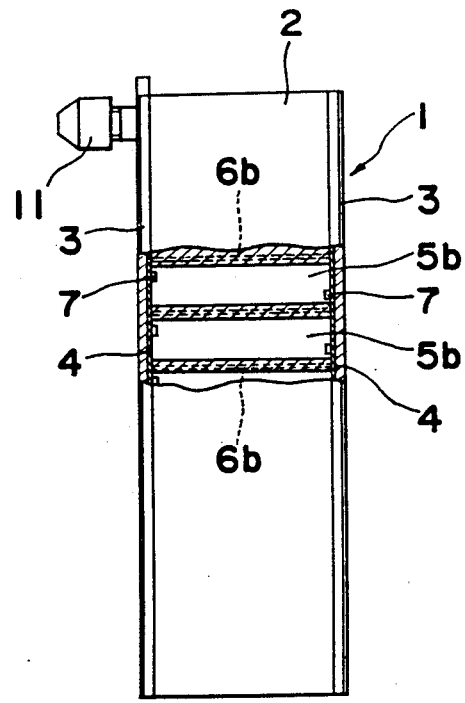
FIG. 17 is a side view, with a portion cut away, of the prior art cassette.
Figure 18:
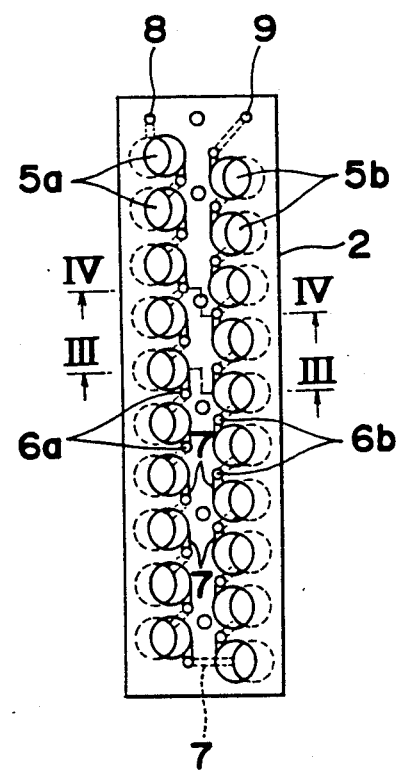
FIG. 18 is a front elevational view of the cassette of FIG. 17 with the sealing plate removed.
Figure 19:
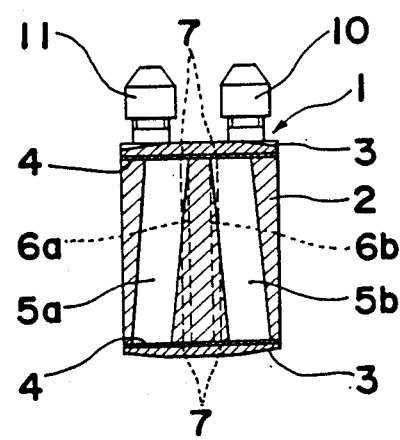
FIGS. 19 and 20 are cross-sectional view taken along the lines III—III and IV—IV respectively in FIG. 18.
Figure 20:
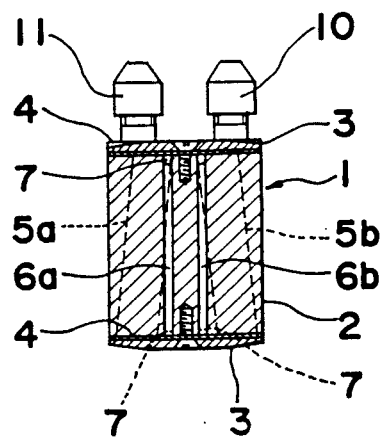

The operation of the apparatus having the construction according to the foregoing embodiment will now be described with particular reference to FIGS. 15 and 16.

At the outset, the tortuous separation passage including the elongated chambers 124, the channels 125 and the connecting ducts 126, is filled with a quantity of stationary phase liquid A having a high specific gravity. Thereafter, a drive motor (not shown) is driven to rotate the rotor 118 at a high speed about the shaft 123 while a mobile phase liquid B is pumped through a supply piping 127 via the rotary coupling 128 so as to flow into the inlet port 121' through the tubing 129 thereby to initiate the counter-current distribution. In other words, the mobile phase liquid B supplied through the inlet port 121' into the narrow channel 125 in the uppermost passage defining member 119 introduces the stationary phase liquid B into the elongated chambers 124 from the outer ends of the channels 125, which are farthest from the shaft 123. Since at this time, a greater centrifugal force acts on the stationary phase liquid A having a high specific gravity than on the mobile phase liquid B having a low specific gravity, the mobile phase liquid B breaks up into fine particles as shown in FIG. 16 moving in a direction counter to the direction in which the centrifugal force acts, that is, in a direction rightwards as viewed in FIG. 16, resulting in a distribution and separation taking place between the mobile phase liquid B and the stationary phase liquid A. At the same time, the particles of the mobile phase liquid B pass through the elongated chambers 124 without being biased, because the elongated chambers 124 are oriented radially of the rotor 118.

The mobile phase liquid B which has passed through the stationary phase liquid A is collected at each inner end face of the elongated chambers 124 and is then centrifugally purged into the channels 125 through the connecting ducts 126. The counter-current distribution is repeated in this way until equilibrium is established. When equilibrium is established, the stationary phase liquid A is retained within the elongated chambers 124 and the mobile phase liquid B fills up the channels 125. In this condition, four fifths of the total volume in the rotor 118 is occupied by the stationary phase liquid A. The mobile phase liquid B which has been fractioned as a result of the passage thereof through the tortuous separation passage is discharged through the tubing 130, then the rotary coupling 131 and finally through a discharge piping 132.

It is to be noted that, while in the foregoing description each groove 119d which eventually forms the respective channel 125 has been described as formed on each of the opposite surfaces of the associated passage defining disc plate 119a, but such may be formed on only one surface of the respective passage defining disc plate 119a.

From the foregoing description, it is clear that, since in the centrifugal counter-current distribution chromatographic apparatus according to the second preferred embodiment the rotor is formed by stacking a plurality of passage defining members, each formed with the slots and the relatively narrow grooves alternating with and open to the slots, with the sealing plates interposed so that the slots and the narrow grooves form the elongated chambers and the channels connected together in an alternating fashion to define the separation passage, a rotor capable of completely separating as many varieties of samples as possible in a time as short as possible can be fabricated by only stacking the passage defining members which can be formed of synthetic resin to have identical shapes by any known molding technique and, therefore, the rotor can be easily and inexpensively manufactured wherefore the cassette can be made available in the market at a reduced price.

Although the present invention has been described in connection with the preferred embodiments thereof with reference to the accompanying drawings, it is to be noted that various changes and modifications will become apparent to those skilled in the art. Such changes and modifications are to be understood as included within the scope of the present invention is defined in the appended claims.

What is claimed is:

1. A method of performing centrifugal countercurrent distribution chromatography, said method comprising:
   providing a centrifuge having a shaft, and a rotor rotatably mounted to and about the shaft, the shaft having a first fluid rotary coupling and a second fluid rotary coupling, and the rotor having at least one pocket extending therein and spaced radially from the shaft;
   operatively connecting the first fluid rotary coupling to a source of at least one fluid sample;
   providing a cassette having at least one flat plate having opposite flat surfaces, a sealing plate covering each of said flat surfaces, and metallic side plates between which said at least one flat plate and each said sealing plate are clamped,
   each said at least one flat plate having a plurality of elongate slots extending in and open to at least one of said flat surfaces and disposed adjacent one another on said at least one of said flat surfaces, and a respective groove extending in said at least one of said flat surfaces between each adjacent pair of said plurality of elongate slots,
   each of said elongate slots extending parallel to one another and in a direction of elongation, from a first end thereof to a second end thereof, across said at least one of said flat surfaces, said plurality of elongate slots spaced apart from one another on said at least one of said flat surfaces in a direction extending perpendicular to said direction of elongation, each said respective groove open to the first end of one of a said adjacent pair of said elongate slots and the second end of the other of said adjacent pair of said elongate slots, and a tortuous separation passage defined in said cassette along said elongate slots and each said respective groove from a first one of said elongate slots to a last one of said elongate slots;

inserting said cassette into the pocket of the rotor with said direction of elongation of each of said slots extending radially with respect to the shaft of the centrifuge, said direction in which said elongate slots are spaced from one another on said at least one of said flat surfaces extending parallel to the shaft of the centrifuge, the first ends of each of said elongate slots being disposed radially outward of the second ends thereof with respect to the shaft of the centrifuge;

placing the first end of said first one of said elongate slots in fluid communication with the first rotary coupling of the shaft of said centrifuge;

placing the last one of said elongate slots in fluid communication with the second rotary coupling of the shaft of the centrifuge;

filling the tortuous separation passage defined in said cassette with a stationary phase liquid;

rotating the rotor of said centrifuge;

selecting the at least one fluid sample to include a mobile phase liquid having a specific gravity lower than that of the stationary phase liquid; and forcing the mobile phase liquid through the tortuous separation passage defined in said cassette via the first fluid rotary coupling as the rotor rotates.

2. A method as claimed in claim 1, wherein said step of operatively connecting the first rotary coupling to a source of at least one fluid sample comprises operatively connecting the first fluid rotary coupling to a source of fluid samples, said step of selecting the at least one fluid sample comprises selecting the at least one fluid sample to include both the stationary phase liquid and the mobile phase liquid, and said step of filling the tortuous separation passage comprises forcing the stationary phase liquid into the tortuous separation passage via the first fluid rotary coupling.

* * * * *